United States Patent [19]

Kelson et al.

[11] Patent Number: 4,807,344
[45] Date of Patent: Feb. 28, 1989

[54] MEDICAL SAMPLING NEEDLE REMOVAL AND DISPOSAL DEVICE

[75] Inventors: Lance P. Kelson, 300 N. 5555 W., Ogden, Utah 84404; Ross J. Kelson, Ogden; Allan F. Martin, Tooele, both of Utah

[73] Assignee: Lance P. Kelson, Ogden, Utah

[21] Appl. No.: 107,354

[22] Filed: Oct. 13, 1987

[51] Int. Cl.⁴ .............................................. B65D 25/00
[52] U.S. Cl. ..................................... 29/240; 206/366
[58] Field of Search ................. 29/240, 240.5, 239, 29/280, 282; 206/365, 366; 254/29 A; 81/57.38

[56] References Cited

U.S. PATENT DOCUMENTS

| | | |
|---|---|---|
| 3,469,750 | 9/1969 | Vanderbeck . |
| 3,851,555 | 12/1974 | Eldridge et al. . |
| 4,255,996 | 3/1981 | Choksi et al. . |
| 4,275,628 | 6/1981 | Greenhouse . |
| 4,375,849 | 3/1983 | Hanifl ................................. 206/366 |
| 4,569,258 | 2/1986 | Orban ................................ 81/57.38 |
| 4,667,821 | 5/1987 | Shillington ........................ 206/366 |
| 4,738,362 | 4/1988 | Burns et al. ....................... 206/366 |

Primary Examiner—Robert C. Watson
Attorney, Agent, or Firm—A. Ray Osburn

[57] ABSTRACT

A device for removing and disposing of blood sampling needles with a minumum of manipulation and without manual contact with any contaminated part. An electrical motor operates a cog wheel to unscrew the needle from the vacuum container sleeve to drop into a closed disposal receptacle. The motor is initiated by depression of a starting switch by the sleeve. The cog wheel is recessed for unimpeded insertion of the needle and sleeve for needle removal. A cycle control circuit assures that the wheel stops in the proper position with the recess adjacent the needle insertion site.

25 Claims, 5 Drawing Sheets

MEDICAL SAMPLING NEEDLE REMOVAL AND DISPOSAL DEVICE

BACKGROUND OF THE INVENTION

1. Field

The field of the invention is the safe of medical needles used to withdraw body fluids, and more particularly the disposal of such needles and associated contaminated items.

2. State of the Art

Several manually and electrically powered devices have been proposed for the destruction of used syringe needles. Some destroy only the cannula (needle), shearing it off and depositing it into a receptacle for discard. Others also destruct the plastic hub of the needle and portions of the syringe barrel. See U.S. Pat. Nos. 3,469,750, 4,255,996, 3,851,555 and 4,275,628. All provide receptacles for the severed needles, hubs and other destroyed parts of the syringe. The contaminated syringe bodies must be separately placed in the disposal receptacles when these devices are used, although U.S. Pat. No. 3,469,750 refers to a device which crushes the entire syringe assembly. It is noted that this device is very heavy, stationary and not portable. The large force required is felt to be potentially dangerous.

Blood samples are now generally taken not with syringes for subsequent transfer to a sample container such as a test tube, but directly into such a container. This container is evacuated, sealed by an elastic plug, and placed seal first into an elongate barrel sleeve open at one end and narrowed to a threaded nipple at the other. A double ended tubular sampling needle (cannula) is mounted on a central hub threaded to fit the nipple. The outside end of the cannula is inserted into a vein. The sealed end of the evacuated container is then pressed against the other, inside, end of the needle, puncturing the resilient plug and allowing the internal vacuum to draw the blood sample through the needle into the container. After the needle is withdrawn from the vein, the container is withdrawn from the needle, leaving the sample inside. The sleeve may be safely reused since it never contacts the blood or the body of the patient. However, there is presently no method of removing the needle from the barrel without excessive manipulation and attendant danger of injury and infection to the medical technician. Typically, a needle disposal receptacle is provided with a lid having an aperture shaped to engage the needle hub. The technician, who most often has one hand engaged with the patient's needle wound, must very carefully insert the needle into the narrow opening with the other. Then, he must grip, release and regrip the sleeve several times while rotating it to unscrew it from the needle hub, all with a single hand. It is difficult to perceive when the needle is completely disengaged, and the needle even then tends to hang up in the opening. Danger of injury from the contaminated needles is considerable.

BRIEF SUMMARY OF THE INVENTION

With the foregoing in mind, the present invention eliminates or substantially alleviates the shortcomings and disadvantages of the prior art by removing virtually all the manual manipulation now required to remove and dispose of double ended fluid sampling needles used with evacuated sample containers. The device comprises a rotating wheel adapted to engage the hubs of the needles, an electrical motor to provide torque to the wheel, either directly or through appropriate gears, and electrical switching and control means. Advantageously, these components are all mounted upon a base adapted to be secured to the mouth of a disposal receptacle for the used needles. After the specimen container is removed, the container sleeve is positioned in the device, the needle and hub being inserted through an aperture provided through the base. The hub is then unthreaded from the sleeve by the wheel, and then drops into the receptacle.

In the preferred embodiment, the rotating wheel is powered by a two phase unidirectional stepper motor, along with a pulse generating timer circuit and motor controller (chip). The stepper type motor is preferred because it builds very quickly to full torque, and also because it stops promptly without appreciable coasting when electric power to it is interrupted. The needle engaging periphery of the wheel may be recessed in at least one location to provide clearance for inserting the needle for removal. A spring loaded, normally open, initiation switch is pressed by the vacuum container sleeve to start the motor. A cam operated cycle control switch assures that the motor is always stopped with the wheel in proper position for the next use. Parallel arrangement of the initiation and cycle control switches assures the continued operation as long as the former is held in depressed, closed position. Direct current batteries are provided in one embodiment. In another, a transformer/rectifier is used with an alternating current source. Batteries, if used, may be mounted upon the above mentioned plate. In this case, it is advantageous to employ rechargeable batteries and appropriate recharging circuitry. Since the needle hubs commonly carry cruciform, gear-like knurls, the hub engaging wheel advantageously carries cogs on its circumference, although knurls or other high friction constructions may also be used.

It is therefore the principal objective of the invention to provide a device for the disposal of used medical cannulae without danger of injury of infection to the medical technician, nurse or doctor.

BRIEF DESCRIPTION OF THE DRAWINGS

In the drawings, which represent the best mode presently contemplated for carrying out the invention.

DETAILED DESCRIPTION OF ILLUSTRATED EMBODIMENTS

Figure 1:
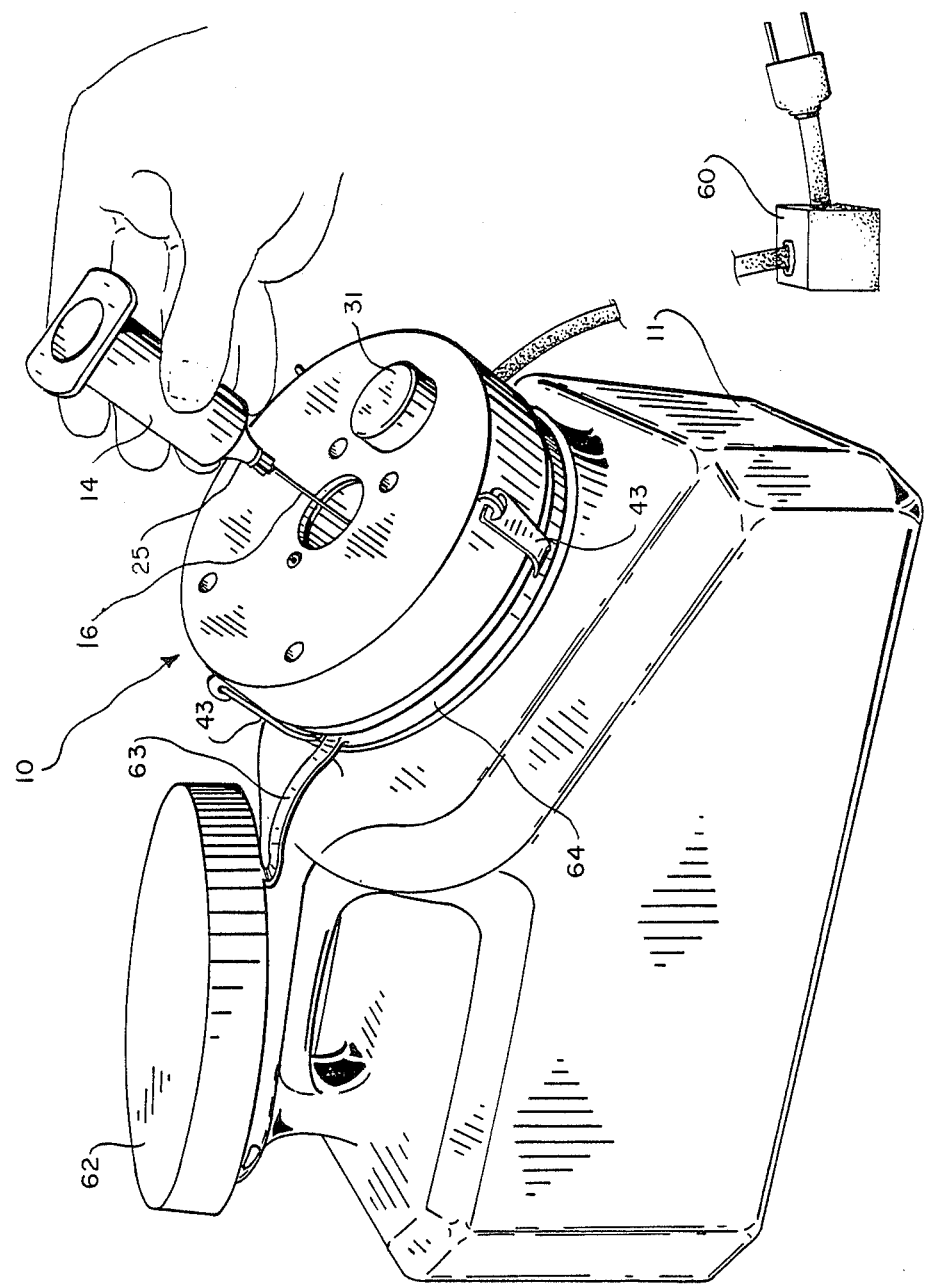
FIG. 1 is a perspective view of the needle remover and disposal device secured to the mouth of a needle disposal receptacle, drawn to a somewhat reduced scale, FIG. 2 a blood sample taking assembly including an evacuated sample container, a double-ended cannula and the sleeve initially holding the sample container, partially cut away, drawn to substantially full scale, FIG. 3 a vertical cross sectional view of the needle removal device of claim 1, taken along line 3—3 thereof, and including the sample container sleeve and the double-ended cannula being removed therefrom, drawn substantially full scale, FIG. 4 a vertical sectional view of a fragment of the needle remover of FIG. 6, taken along line 4—4 thereof, showing the cycling switch, and the associated cam, drawn to substantially full scale, FIG. 5 a top view of the needle remover of FIG. 3, taken along line 5—5 thereof, the cover being cut away to show the control panel, the batteries, and the cycle control switch, drawn to substantially full scale, FIG. 6 a sectional view taken along line 6—6 of FIG. 5, drawn to the same scale, FIG. 7 a view, of the bottom of the needle remover of FIG. 3, taken along line 7—7 thereof, drawn to the same scale, FIG. 8 a view of the top of the cog wheel of FIG. 6, taken along 8—8 thereof, drawn to the same scale, FIG. 9 an enlarged view of a fragment of FIG. 7 showing the cogs in engagement with the knurls of the needle hub, FIG. 10 a schematic view of the power and control system operating the motor of the needle removal device, and FIG. 11 a schematic representation of an alternate system of cogs or wheels to unscrew the needle from the sleeve.
Figure 2:
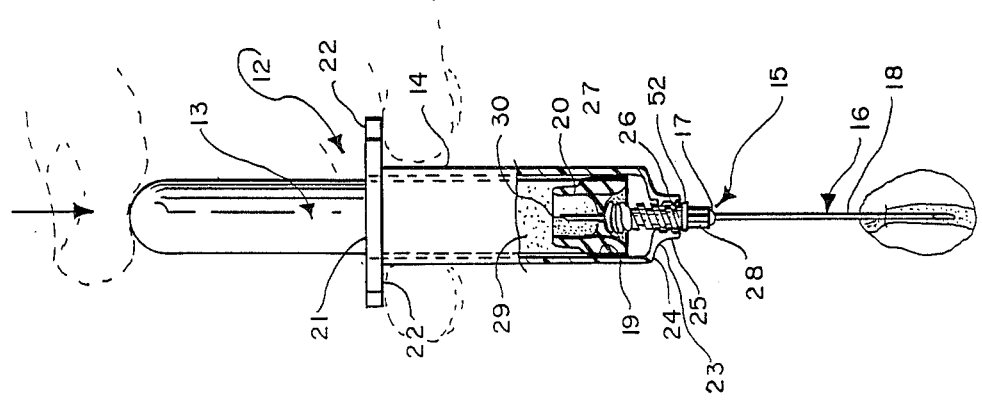

In FIG. 1, needle remover 10 is secured in place of a lid upon a used-needle receptacle 11. An assembled vacuum container blood sampling device 12 is shown in FIG. 2. Sampler assembly 12 comprises an evacuated specimen container 13, a container sleeve 14, and a sampling needle assembly 15. Needle assembly 15 includes double-ended tubular cannula 16 secured within a central hub 17. Outside portion 18 of cannula 16 is indicated as inserted into a vein. The evacuated sample container 13 is closed at its open end 19 by an elastic seal 20, preserving the internal vacuum until time of use. Sleeve 14 has an open end 21 with a pair of graspable ears 22. Its opposite end 23 narrows through a shoulder 24 of a nipple 25 with internal threads 26. Threads 26 accept external threads 27 on hub 17. Hub 17 is typically provided with cruciform knurls 28, which are gripped to engage hub 17 to nipple 25.

Figure 3:
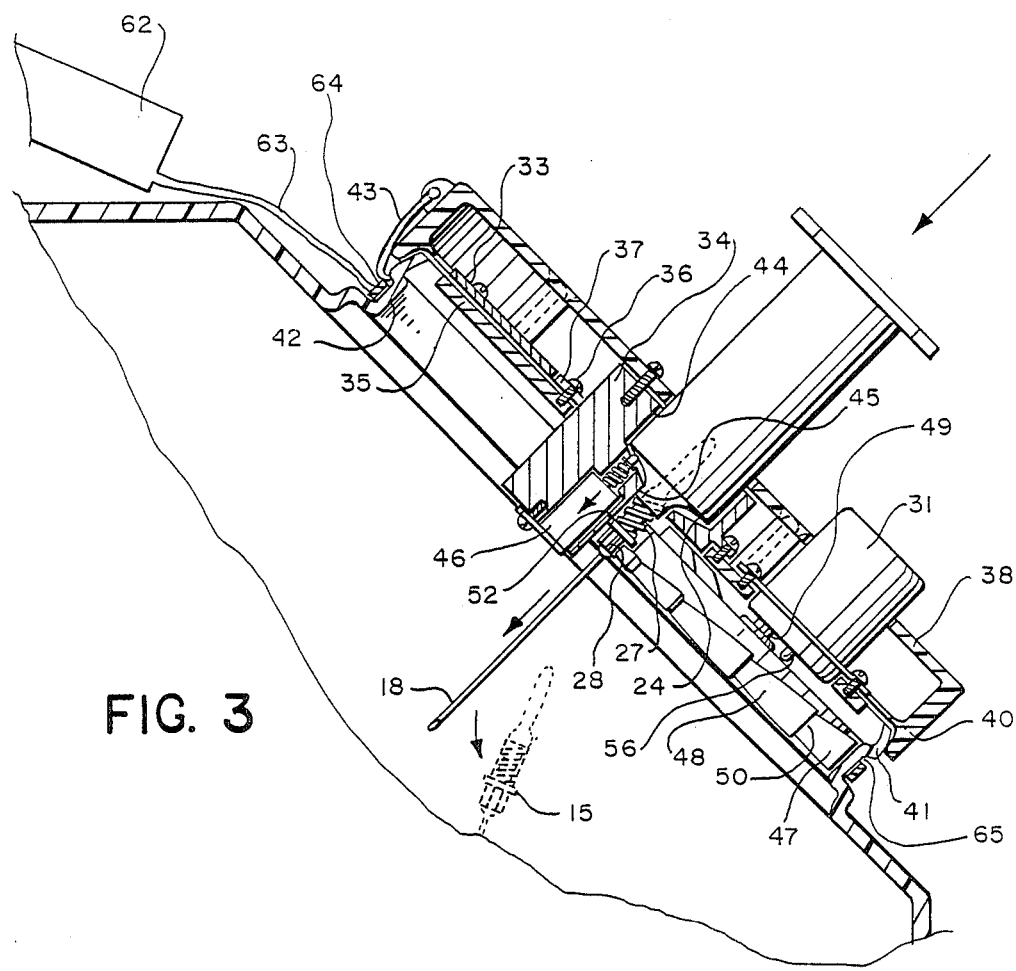

To take a blood specimen 29, outside needle 18 is first inserted into the vein. Then, vacuum container 13 is pressed into sleeve 14, puncturing seal 20 on inside end 30 of cannula 16. The internal vacuum draws the sample 29 into container 13. Specimen container 13 is then withdrawn from sleeve 14, punctured closure 20 contracting elastically to close the seal. Needle 18 and sleeve 14 are then withdrawn together, and inserted into remover 10 as shown in FIGS. 1 and 3.

Figure 5:
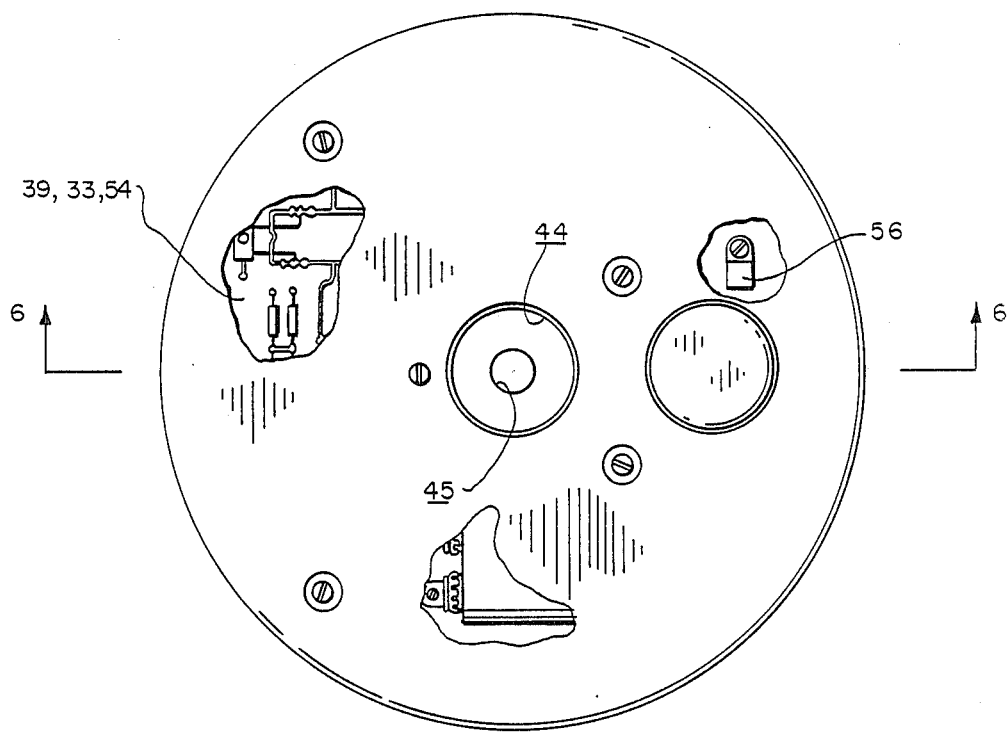

Needle remover 10 comprises a direct current stepper motor 31 (such as Haydon Switch & Instrument, Inc., series 33700), batteries 32, a motor controller (chip) 33 (FIG. 5 and 10) and a needle insertion block 34, all mounted upon a base plate 35. Screws 36 act through tabs 37 to secure needle block 34 to plate 35. Cover 38 is apertured to accommodate motor 31, and needle insertion block 34. Motor controller 33 is installed upon a panel assembly 39, with other circuit elements described hereinafter. Panel 39 is secured to base plate 35 beneath cover 38. Cover rim 40 is preferably shaped to fit upper rim 41 of receptacle mouth 42. Spring clips 43 secure cover 38 and the entire assembly 10 detachably to receptacle 11.

Needle insertion block 34 has a sleeve insertion bore 44 concentric with a nipple-accepting bore 45. An initiation switch 46 in needle block 34 is spring loaded to normally open position. It is actuated by the tapered shoulder 24 of vacuum container sleeve 14, causing motor 31 to operate.

Cogs 47 of wheel 48 on output shaft 49 of motor 31 engage knurls 28 of needle hub 17. (FIGS. 3 & 6-9) A cog free recessed portion 50 allows unimpeded insertion of needle end 18, sleeve nipple 25 and needle hub 17 through needle block bore 44 and nipple bore 45. As subsequently described, wheel 48 is made to stop with recess 50 adjacent to nipple bore 45 after each use of needle remover 10.

When switch 46 is closed by shoulder 24 of sleeve 14, motor 31 rotates cog wheel 48 to engage knurls 28 by the teeth 47 to unscrew needle assembly 15 from nipple 25. Clearance above cog teeth 47 varies progressively along wheel periphery 51, to avoid binding with hub 17 as it is screwed progressively out of nipple 25. When hub threads 27 are free of nipple threads 26, needle assembly 15 falls into receptacle 11 as hub knurls 28 immediately disengage from cogs 47. If hub flange 52 hangs up on the upper sides 53 of cogs 47, it is freed by continued rotation of wheel 48, recess 50 then coming into position to provide ample clearance.

Figure 10:
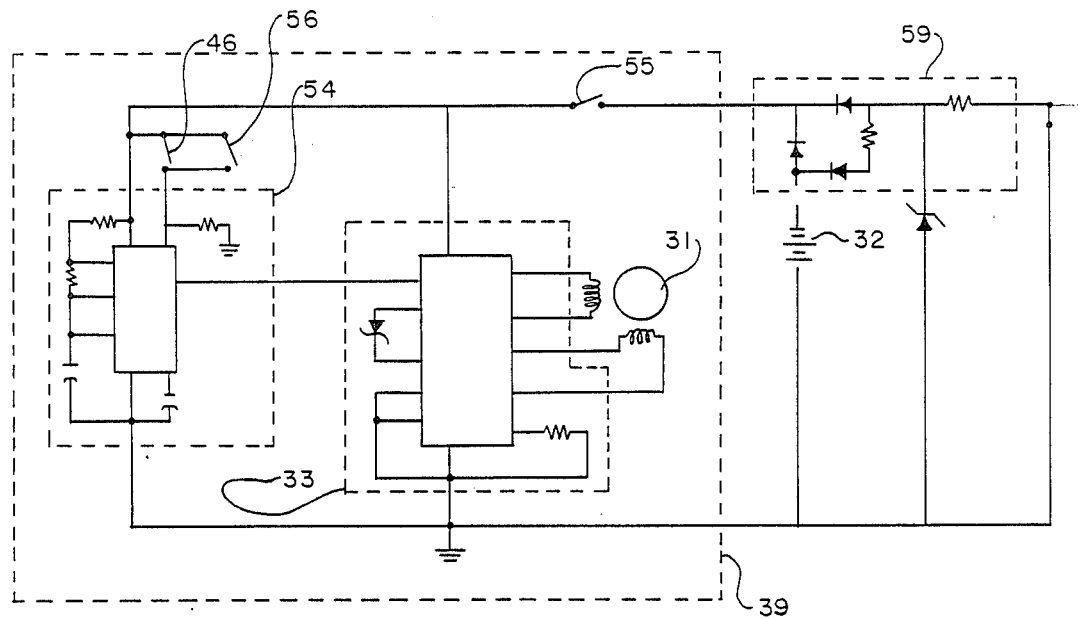

When sample container sleeve 14 is removed from bore 44, motor 31 does not stop until wheel 48 is rotated to bring recess 50 into position for the next use of device 10. Electrical schematic FIG. 10 illustrates a preferred electrical control system. Key elements of the system are provided in control panel assembly 39. Motor controller circuit 33 passes current to DC stepper motor 31 from a source of direct current power, e.g. batteries 32. Controller 33 is programmed to pass current upon command signals from a timing circuit ("clock") 54 which, advantageously, may be a square wave pulse generator.

Figure 4:
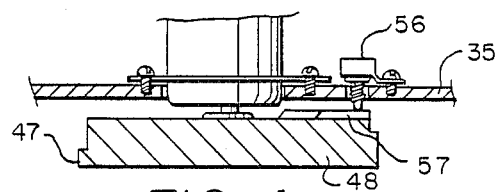
Figure 6:
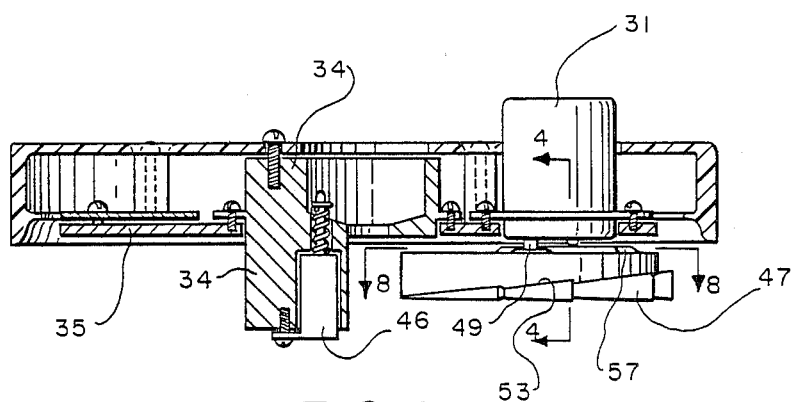
Figure 7:
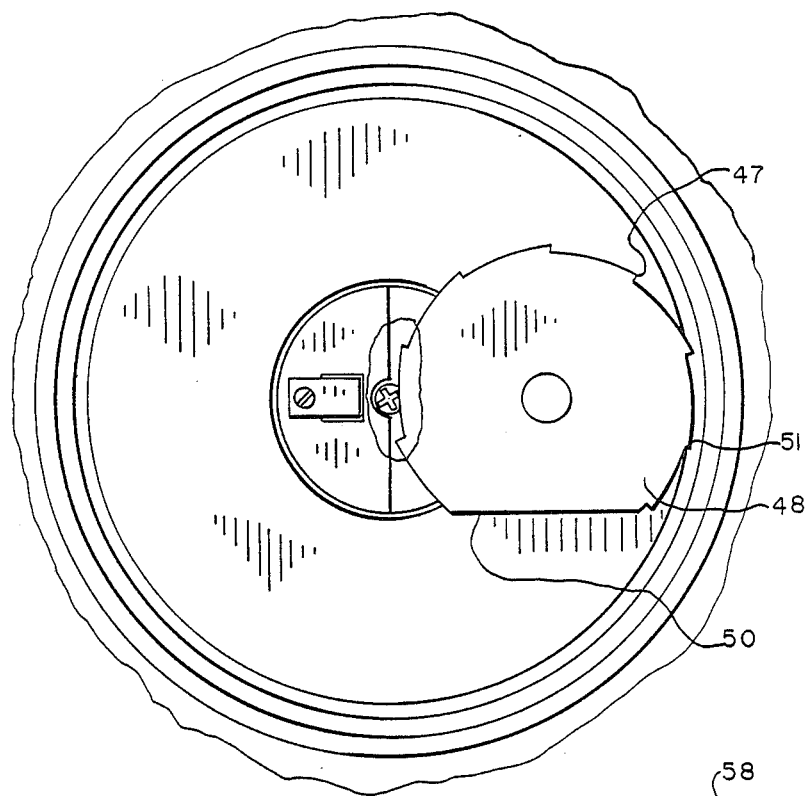
Figure 8:
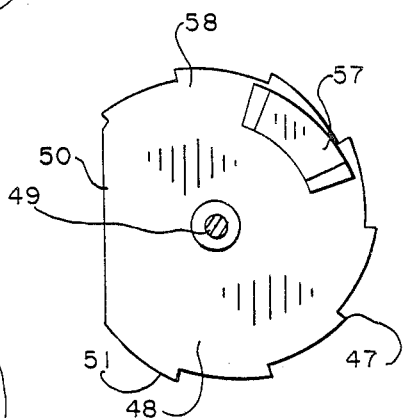
Figure 9:
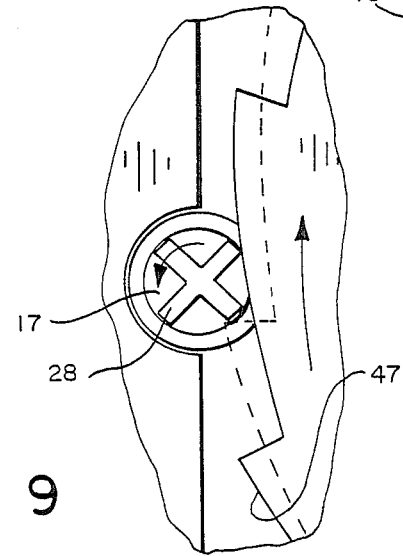

Closing of power supply switch 55 readies needle remover 10 for use. Depression of initiation switch 46 activates clock 54 to generate evenly spaced periodic command signals to motor controller 53. As long as initiation switch 46 is held in closed position by shoulder 24 of sleeve 14, motor 31 continues to operate, rotating cog wheel 48. A cycle control switch 56 is connected in parallel to initiation switch 46. Spring loaded, normally closed switch 56 is mounted on base plate 35, and is controlled by a cam 57 ramped upwardly from top surface 58 of cog wheel 48. (FIGS. 4, 6 and 8)

When initiation switch 46 is released to open, still closed cycle switch 56 causes motor 31 to continue turning until recess 50 is in proper position adjacent the needle removal site. (FIG. 8) In this position, cam 57 opens cycle switch 56, stopping motor 31 and cog wheel 48.

A circuit 59 may be provided for recharging batteries 32. (FIG. 10) This recharging circuit may be provided separately if too large or heavy for mounting upon base plate 35. Or, if desired because of such mounting restraints, a separate DC rectifier/transformer power pack 60 may be provided in lieu of the batteries 32. (FIG. 1)

Figure 11:
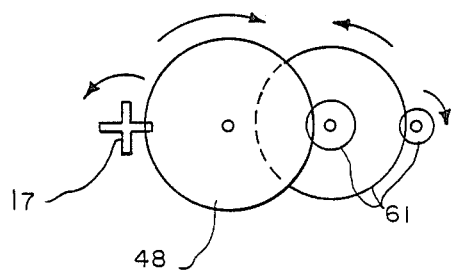

Other changes may be made to the illustrated preferred embodiment of the needle removal device 10 without departing from the spirit of the invention. The wheel 48 could be mounted to revolve about an axle provided on plate 35, to be driven by a train of two or more gears 61. (FIG. 11) The cogs 47 could be replaced with, e.g., a wheel periphery adapted to unscrew hub 17 by friction. Electrical motors 31 other than the preferred DC stepper type described could, with suitable gearing and control features, be utilized, although with sacrifice of simplicity, economy, weight and portability.

To dispose of receptacle 11 with accumulated contaminated needles, needle remover 10 is detached from container mouth 42 by release of spring clamps 43. Advantageously, an auxiliary lid 62 is provided secured by flexible strip 63 to a retainer band 64 about receptacle opening 42. Auxiliary lid 62 snaps into mouth groove 65. (FIGS. 1 and 3) Needle remover 10 may be quickly installed by clamps 43 upon a new receptacle 11. Device 10 may also be adapted for use with other sizes and types of used needle receptacles.

The invention may be embodied in other specific forms without departing from the spirit or essential characteristics thereof. The present embodiments are therefore to be considered as illustrative and not restrictive, the scope of the invention being indicated by the appended claims rather than by the foregoing description, and all changes that come within the meaning and range of equivalency of the claims are therefore intended to be embraced therein.

What is claimed and desired to be secured by United States Letters Patent is:

1. A device for safely removing a medical cannula from a body fluid sampling assembly said cannula being mounted within an externally threaded hub, an external sleeve, and an internally threaded boss carried by the sleeve and engaging the threads of the hub, said removal device comprising:
    a base plate having an upper side and a lower side;
    an electrical motor mounted on the base plate and having a rotating output shaft;
    a wheel mounted to be rotated by the shaft;
    hub engaging means on at least a portion of the periphery of the wheel; and
    means positioning the sleeve for engagement of the hub by the periphery of the wheel, so that the hub is rotated to be unthreaded from the assembly.
2. The device of claim 1, further comprising:
    a normally open initiation switch controlling the operation of the motor, and positioned to be closed by contact with the sampling assembly when it is placed into the device for removal of the cannula.
3. The device of claim 2, wherein:
    the device is configured so that the cannula and hub fall below the base plate when the hub is unthreaded from the sampling assembly.
4. The device of claim 3, further comprising:
    means securing the device to the mouth of a used cannula disposal receptacle.
5. The device of claim 2, wherein:
    the periphery of the wheel has at least one recess providing clearance for unimpeded placement of the sampling assembly into the device for removal of the cannula; and the device further includes
    indexing control means causing the wheel to stop rotating after each use with said recess in position for such placement.
6. The device of claim 5, wherein the indexing control means comprises:
    a normally closed cycle control switch connected in parallel with the initiation switch; and
    a cam closing the cycle control switch at a rotated position of the wheel in which the recess is in position for the next use of the device.
7. The device of claim 6, wherein:
    the motor is a direct current stepper type motor.
8. The device of claim 7, further comprising:
    a control unit for passing current to the motor in response to an electrical command signal; and
    an electrical circuit for generation of time spaced electrical command signals to the control unit, said signal generating circuit being controlled by the initiation and cycle control switches.
9. The device of claim 8, further comprising:
    a source of direct current electrical power.
10. The device of claim 9, wherein:
    the direct current power source is at least one direct current battery.
11. The device of claim 10, wherein:
    the device is configured so that the cannula and hub fall below the base plate when the hub is unthreaded from the sleeve.
12. The device of claim 11, further comprising:
    means securing the device to the mouth of a used cannula disposal receptacle.
13. The device of claim 8, wherein:
    the direct current battery, the signal generating circuit, the initiation and cycle control switches, the motor control unit, and the sleeve positioning means are carried by the base plate.
14. The device of claim 10, further comprising:
    an alternating current powered direct current battery recharging circuit.
15. The device of claim 13, further comprising:
    an alternating current powered direct current battery recharging circuit.
16. The device of claim 15, wherein:
    the recharging circuit is mounted upon the base plate.
17. The device of claim 9, wherein:
    the direct current power source is an alternating current transformer and rectifier circuit.
18. The device of claim 17, wherein:
    the transformer and rectifier circuit, the signal generating circuit, the initiation and cycle control switches, the motor control unit, and the sleeve positioning means are carried by the base plate.
19. The device of claim 5, wherein:
    the wheel is secured directly to the output shaft of the motor.
20. The device of claim 6, wherein:
    the wheel is secured directly to the output shaft of the motor.
21. The device of claim 8, wherein:
    the wheel is secured directly to the output shaft of the motor.
22. The device of claim 21, wherein:
    the cam is located upon the wheel.
23. The device of claim 5, further comprising:
    a wheel axle mounted upon the base plate; and
    a gear train mounted to act between the shaft and the wheel.
24. The device of claim 6, further comprising:
    a wheel axle mounted upon the base plate; and
    a gear train mounted to act between the shaft and the wheel.
25. The device of claim 8, further comprising:
    a wheel axle mounted upon the base plate; and
    a gear train mounted to act between the shaft and the wheel.

* * * * *